United States Patent [19]
Hiatt

[11] Patent Number: 5,411,707
[45] Date of Patent: May 2, 1995

[54] VACUUM EXTRACTOR INCORPORATING A CONDENSER COLUMN

[75] Inventor: Michael H. Hiatt, Las Vagas, Nev.

[73] Assignee: The United States of American as represented by the Administrator of the Environmental Protection Agency, Washington, D.C.

[21] Appl. No.: 180,518

[22] Filed: Jan. 12, 1994

Related U.S. Application Data

[63] Continuation of Ser. No. 904,100, Jun. 25, 1992, abandoned.

[51] Int. Cl.[6] ............ G01N 30/02; G01N 30/12; G01N 30/14
[52] U.S. Cl. .................. 422/68.1; 422/83; 422/89; 436/161; 436/177; 96/101; 73/23.41
[58] Field of Search ............ 422/89, 68.1, 83, 81; 436/161, 177, 181, 158; 96/101; 73/23.41; 202/205, 182; 203/DIG. 2

[56] References Cited

U.S. PATENT DOCUMENTS

| | | | |
|---|---|---|---|
| 2,476,477 | 7/1949 | Berg | 203/DIG. 2 |
| 3,240,682 | 3/1966 | Gordon | 203/DIG. 2 |
| 4,480,039 | 10/1984 | Closmann et al. | 436/177 |
| 4,600,559 | 7/1986 | Hiatt | 422/89 |
| 4,960,711 | 10/1990 | Aoki et al. | 436/124 |
| 5,024,952 | 6/1991 | Alsop | 436/177 |
| 5,065,614 | 11/1991 | Hartman et al. | 73/23.41 |
| 5,152,176 | 10/1992 | Bryselbout et al. | 72/23.41 |

OTHER PUBLICATIONS

Hiatt, Michael H., "Determination of Volatile Organic Compounds in Fish Samples by Vacuum Distillation and Fused Silica Capillary Gas Chromatography/Mass Spectrometry", *Anal. Chem.* 55: pp. 506–516, 1983.

Hiatt, Michael H., "Analysis of Fish and Sediment for Volatile Priority Pollutants", *Anal. Chem.*, 53: pp. 1541–1543, 1981.

Easley et al., "Gas Chromatographic–Mass Spectrometric Determination of Volatile Organic Compounds in Fish", *J. Assoc. Off. Anal. Chem.*, 64(3): pp. 653–656, 1981.

*Primary Examiner*—James C. Housel
*Assistant Examiner*—Jan M. Ludlow

[57] ABSTRACT

Methods and apparatus for vacuum distillation of samples suspected of containing pollutants are disclosed. The vacuum distillation apparatus contains a condenser for separating water and/or another common interfering contaminant. The distilled pollutants are assayed using a gas chromatograph/mass spectrometer.

16 Claims, 2 Drawing Sheets

VACUUM EXTRACTOR INCORPORATING A CONDENSER COLUMN

This is a continuation of application Ser. No. 07/904,100 filed on Jun. 25, 1992, now abandoned.

FIELD OF THE INVENTION

The present invention relates to the separation, isolation, detection and quantification of trace chemicals in a variety of samples using vacuum distillation.

BACKGROUND TO THE INVENTION

In recent years there has been a growing concern over exposure to toxins in the environment and food supply. The Federal Water Pollution Control Act Amendments of 1972 (P.L. 92-500) recognized the need for monitoring and establishing the presence of toxic substances in water. Organic pollutants are frequently present in very small amounts and often comprise a large number of similar compounds which may have been deposited at a particular location through a variety of means. Some of these pollutants are concentrated in the tissues of plants and animals and can be hazardous to these life forms as well as animals, including humans, that eat them. Thus the need exists for accurate measurements of trace amounts of contaminating pollutants.

While conventional chromatography and detection techniques are effective measurers and detectors of organic compounds, the samples to be tested contain the organic compound components in matrixes or are in matrixes which may interfere with the proper extraction and detection of the compound components in questions. Using conventional techniques, it has been difficult to determine certain compounds, to assess the degree of matrix effects on compound recovery and to accurately quantify the amounts of these and other compounds.

Soil, biological samples, oils and water each present their own unique difficulties and interfering chemicals. Techniques prior to, and even after, the vacuum extractor described in applicant's earlier U.S. Pat. No. 4,600,559 have not been particularly effective at detecting an accurate amount of a chemical in certain samples due to low rates of extraction and poor separation. For example, U.S. Pat. No. 4,960,711.

In the prior art, investigators have attempted to measure trace organic compounds by a number of techniques. One method is to sample gas from the head space above a sample in a closed container. The gas sample is then injected into a gas chromatograph for measurement. Details and variations on this technique are described in the following four references:

1. "Interim Method for the Sampling and Analysis of Priority Pollutants in Sediment and Fish Tissue" Environmental Protection Agency, Environmental Monitoring and Support Laboratory, Cincinnati, Ohio, p. 18 and 45-268, Aug. 23, 1977, 2. "Sampling and Analysis for Screening of Fish for Priority Pollutants," "Analysis of fish for Volatile Organics by Head Space Analysis", U.S. EPA, Environmental Monitoring and Support Laboratory, Cincinnati, Ohio p. 14, Aug. 23, 1977, 3. "The analysis of Fish for Volatile Organics by Head Space Analysis" U.S. Environmental Monitoring and Support Laboratory, Cincinnati, Ohio p. 21, 4. Going, "Priority Pollutant Removal from Mine Drainage" Final Report, MRI Contract 4409-L3, Industrial Environmental Research Laboratory, Office of Research and Development, EPA Cincinnati, Ohio.

These methods have several drawbacks. First, the chemical of interest may not readily disassociate from the sample to permit accurate measurement in the gas. Second, water and other volatile compounds frequently interfere with the detection of the compound of interest. If the compound being detected can form an azeotrope, further complications exist. Third, these techniques are only effective for very volatile compounds.

Another existing technique for measurement of trace organic compounds involves pentane extraction of organic compounds from fish as discussed by Pearson et al, *Proc. Royal Soc. Lond. B*, 189: p. 305-332 (1975). This technique has the disadvantage of only measuring compounds which are soluble in pentane, do not react with pentane, are released from the matrix by liquid pentane and do not participate in a chemical reaction with any other compound being extracted by the pentane.

Another standard technique for measurement of trace organic compounds is to purge and trap. According to this technique, the sample is heated and an inert gas is passed through the sample to "purge" volatile compounds from the sample. The gas containing the compounds is passed through a trap which adsorbs the compounds. One such adsorbent is activated charcoal. The adsorbent is then heated to elute the compounds from this trap into a gas chromatograph for detecting and measuring the compounds. One example of this technique is Murray, *Analytical Chim. Acta*, 65 p. 261-270 (1973).

The purge and trap technique also has certain drawbacks as different compounds have variable rates of adsorption on adsorbents. Furthermore, heating the sample may cause degradation of the compounds of interest. The compounds concentrated in the adsorbent may react with each other or degrade because they are in a different matrix than the one from which they were extracted. Also the compounds being tested may polymerize or react with other compounds present to give byproducts, thereby making it difficult to detect the correct compounds present and causing simultaneous detection of compounds which never were in the sample. While the purge and trap technique recovers a wide mix of compounds, it still fails to adequately recover many compounds.

This may be especially true when non-aqueous samples are analyzed. For non-aqueous samples recoveries are further complicated by any additional affinity for compounds of interest to the solid phase over the aqueous phase. Non-volatile compounds are particularly hard to extract and measure accurately using this technique.

Some of the problems with heating a sample and trapping the released compounds have been ameliorated by using a vacuum instead of heat to extract compounds. Examples of this technique are Easley et al, *J. Assoc. Off. Anal. Chem.*, 64(3) p. 653-656 (1981) and applicant's earlier publication, Hiatt, *Analytical Chemistry*, 53: p. 1541-1543 (1981).

Improvements in the purge and trap method have been provided as described in Hiatt, *Analytical Chemistry*, 55: p. 506-516 (1983) and Hiatt, U.S. Pat. No. 4,600,559. These publications disclose a vacuum extractor with cold traps to condense and collect the compounds being measured. While such a system is more effective than conventional techniques, it is cumbersome with plural cold traps and does not readily lend itself to automation. Additionally, this and all other systems permit the measurement of compounds in the gaseous phase only and do not permit measuring the azeotrope phase, the condensed phase or the residue in the sample container. Thus the previous systems are limited in their capabilities.

SUMMARY OF THE INVENTION

It is therefore an object of the present invention to overcome deficiencies in the prior art such as indicated above.

The invention is thus generally directed to a method for detecting and measuring low concentrations of distillable substances using vacuum distillation where water and other compounds are removed by a condenser and gasses are collected in a cryogenic concentrator connected to at least one gas chromatograph, at least one gas chromatograph/mass spectrometer or other analytic detector(s) such as atomic adsorption, HPLC, ICP, SCFE, etc.

It is a further object of the present invention to provide a simplified method and apparatus for detecting and quantifying a low boiling point or volatile compound in a sample.

It is yet another object of the present invention to provide a system with less physical steps and simpler design for ease of manufacture and use.

It is still another object of the present invention to provide a system which can be automated to analyze multiple fractions from a sample without cumbersome and labor intensive techniques.

It is still a further object of the present invention to provide a system which can analyze multiple samples without extensive efforts at preparing the system for each sample, each time.

It is yet a further object of the present invention to provide a system which will recover a high percentage and/or reproducible data for various compounds from a sample for accurate quantification.

It is yet another object of the present invention to be able to accurately measure compounds from samples which have high amounts of interfering compounds.

It is still yet another object of the present invention to fractionate distillates as a gas phase condensates and residual sample for subsequent analyses.

These objects of the present invention are achieved with a vacuum distillation apparatus and gas chromatograph (GC) with one or more detectors such as a mass spectrometer (MS). A condenser column is placed between a chamber containing a sample and the vacuum source. The condenser column is heat regulatable and will remove water or other common component thereby facilitating the easy detection of trace compounds. Gases which pass through the column are trapped in a cryotrap at very cold temperatures. The contents of the cryotrap are later transferred using an inert carrier gas and analyzed by the GC or GC/MS. Appropriate gas or gas containing compounds flow in the system is controlled by a multiport valve or series of valves, such as a single six port valve to alternate between vacuum distillation/collection of gases and driving samples to the gas chromatograph.

DESCRIPTION OF THE PREFERRED EMBODIMENT

The described invention is used for detecting compounds, particularly various environmental pollutants in an assortment of samples such as water, soil, sediments, oils, life forms such as fish, shellfish microbes etc., their fluids and tissues. The samples may be in any form such as liquid, solid, oily wastes, sludges etc. The present method and apparatus may also be used to quantify such pollutants in food and feed products and components used therefore. Analytical detection of trace quantities of desired or undesired compounds is also useful in connection with the production of pharmaceuticals, medical supplies, and a wide assortment of consumer and industrial goods.

While the examples refer to organic compounds; organometallic, inorganic compounds and compositions of variable composition may also be detected provided that such compounds are sufficiently volatile or have a low boiling point. Suitable examples include methyl mercury, sulfur chloride and phosphorous trichloride. Compounds which are best detected are those with a boiling point below 180° C. and are insoluble or slightly soluble in water. Non-volatile compounds which typically boil under 200° C. are also analyzable using the method and apparatus of the invention. Such compounds include: amines, semivolatiles, alcohols, ketones, aldehydes, phenols, nitrosamines, and other aromatic compounds. Compounds very soluble in water may also be tested using the present invention, but depending on the quantity, the size of the cryotrap may have to be adjusted to accept large volumes of distillate.

The sample may be pretreated to permit easier purging of detectable compounds. Pretreatment techniques include drying, physical disruption such as grinding, chemical disruption, photoactivation, and removal of contaminants from the sample.

Figure 1:
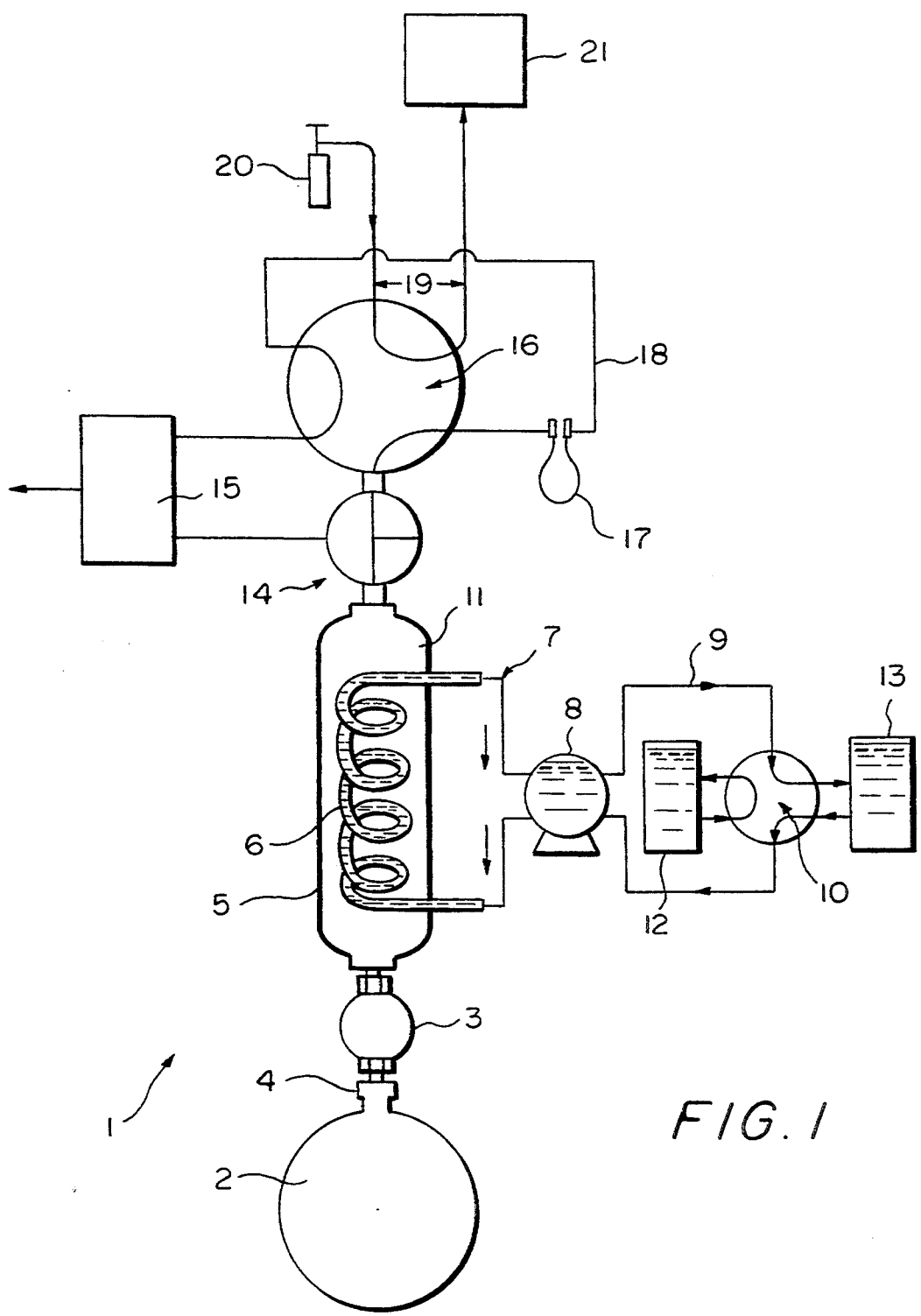
FIG. 1 is a schematic elevational view of the novel apparatus of the invention in the loading position and the condenser fluid is adjusted to a cooling means.

In the apparatus shown in FIG. 1, a vacuum distillation-detector system 1 is shown in the loading position. The sample is placed in a container which becomes the sample chamber 2 of the system. The sample chamber 2 is connected to the remainder of the system through sample chamber valve 3. An air tight seal 4 may be located on either the sample chamber or the sample chamber valve and the valve may be removable from both. The sample chamber valve may be a simple on/off valve. A plurality of sample chambers may be used, in which each of the sample chambers are connected to the remainder of the system using a more complex sample chamber valve system or series of systems. This configuration lends itself to an automated design in which samples may be sequentially analyzed.

The sample chamber valve(s) 3 are fluidly connected to a condenser 5 which contains a coil 6 or other configuration to provide temperature regulation within the condenser 5. The coil or other means for heating and cooling the condenser may also be external to the condenser to cool or heat it. One or more heat conducting loops or other configurations around or protruding into the condenser may also be used to regulate temperature. The design of the condenser need not be the simple tubular design shown in FIG. 1 but may involve a tortuous pathway for the gas to flow across various surfaces to modify gas temperature and provide additional surface area for condensation. Multiple coils or the like may be used, each maintaining the same or applying a different temperature.

The purpose of a condenser is to condense or freeze certain compounds in the condenser so that they do not pass through to the detector. Examples of compounds one may want to remove in the condenser include common compounds in the sample, such as water, and known or suspected interferants.

In FIG. 1, the coil 6 is hollow with fluid flowing through it. Alternatively, electrically conductive material and/or thermally conductive material may be used to regulate temperature. Other materials (not shown) may be added to the condenser to provide surface area to increase the degree of separation of gases at the temperature desired. A collection system (not shown) for liquids condensed on the coil or other surfaces in the condenser may be used to withdraw the liquids and/or separate these liquids for a separate analysis. Additional adsorbents particular for a common interfering compound(s) may also be added to the condenser column or elsewhere in the system to at least partially remove such interference.

The condenser may include a catchment area in the bottom of the column to automatically prevent condensed liquids from returning to the sample chamber. This catchment area may conveniently contain a port whereby liquid may be withdrawn for separate analysis. This liquid may have its compounds detected by the same or additional detection means, such as direct injection into a gas chromatograph.

One means of temperature regulation involving fluid flowing through coil 6 includes using a pump means 8 to cause fluid flow 7 through the coil 6. The arrows in FIG. 1 indicate one possible direction of fluid flow. An isovolume pump, such as a peristaltic pump, is desirable because of its fine control of flow rates, but other pumping means are acceptable.

To regulate the temperature inside the condenser, the condenser fluid uses a temperature altering system of any configuration which can preferably both heat and cool the fluid to any desired temperature. An illustrated method for performing such acts is to pump condenser fluid through line 9 to a valve 10 which flows the fluid to either heating means 12 or cooling means 13 before being recirculated to the condenser. It is anticipated that the pump means 8 may be located at any point in the condenser fluid loop. FIG. 1 arbitrarily shows fluid flow through a cooling means 13 and FIG. 2 arbitrarily shows fluid flow through a heating means 12. It is contemplated that neither is particularly associated with either the loading or the injection position and is separately adjustable.

The choice of whether to heat or cool the condenser fluid the rate of heating or cooling, and rate of fluid flow will depend on the desired temperature inside the condenser, the type and amount of sample, the size and design of the apparatus and the effectiveness of the vacuum pump. In addition to monitoring the condenser, a thermometer or thermocouple 11 may be added and all of the parameters continuously or intermittently measured to provide finer control of the system. Also, thermometers or thermocouples may be placed in the circulating condenser fluid at various places, in the sample chamber and in the loop 18 to finely measure the temperatures in the system. Pressure gauges, such as Pirani gauges, may likewise be placed in the sample chamber, the condenser, just before the vacuum pump and in the loop to monitor the pressure. Measurements may be sent to a computer which compares the values received to a set of desired circumstances and issues appropriate corrective commands to adjust the valves, pumps etc. for optimal performance. It is contemplated that the entire method from placing the sample in a container to composition analysis of the readout from a detector may be automated to reduce human labor, the potential for human error and increase precision by closer reproduction of conditions.

The choice of fluids to use in the condenser 5 is wide and limited only by the heating and cooling needs of the condenser. The selection of suitable gasses or liquids are readily apparent to those skilled in the art based upon the heating and cooling needs, condenser and coil size and heating and cooling means.

At the opposite end of the condenser from the sample chamber valve 3 is a vacuum pump valve 14 which connects the gas flow to a vacuum pump 15 or connects the flow to a sampling valve 16 through a cryotrap 17 and then via loop 18 to a detection system 21. A cold trap or other suitable means (not shown) may be located near the vacuum pump in order to prevent water from reaching the pump oil which affects pump vacuum efficiency and to prevent pump oil vapors from contaminating the gas sample. Gases from the vacuum pump are exhausted to the air or a hood.

When the vacuum pump valve 14 is open to the sampling valve 16, the gas flow passes through the valve to a cryotrap 17 which is kept at very low temperatures to condense any chemicals being volatilized from the sample during vacuum distillation. Two or more cryotraps may be used in parallel so that different fractions of distillate may be trapped and analyzed separately. The preferred nature of the sampling valve 16 is a multiport valve, especially a six port valve. When multiple cryotraps are used, a higher number of ports will be needed if each cryotrap were to have only one valve. One such example is a 10 port valve. Other configurations or a plurality of valves may be used provided that the valves are changed at the same time without significant delay. When multiple cryotraps are used, it may be advantageous to employ multiple detectors 21 as different fractions may best be separated and/or detected by different means. Alternatively, a detector operating by different ways, such as a GC with two different columns may be employed. Gasses not trapped by the cryotrap 17, such as nitrogen, oxygen etc. travel through loop 18 to the vacuum pump 15. Again, a cold trap (not shown) to prevent contamination of vacuum pump oil vapors may be employed. This is the basic configuration during the purging of volatile compounds from the sample.

Figure 2:
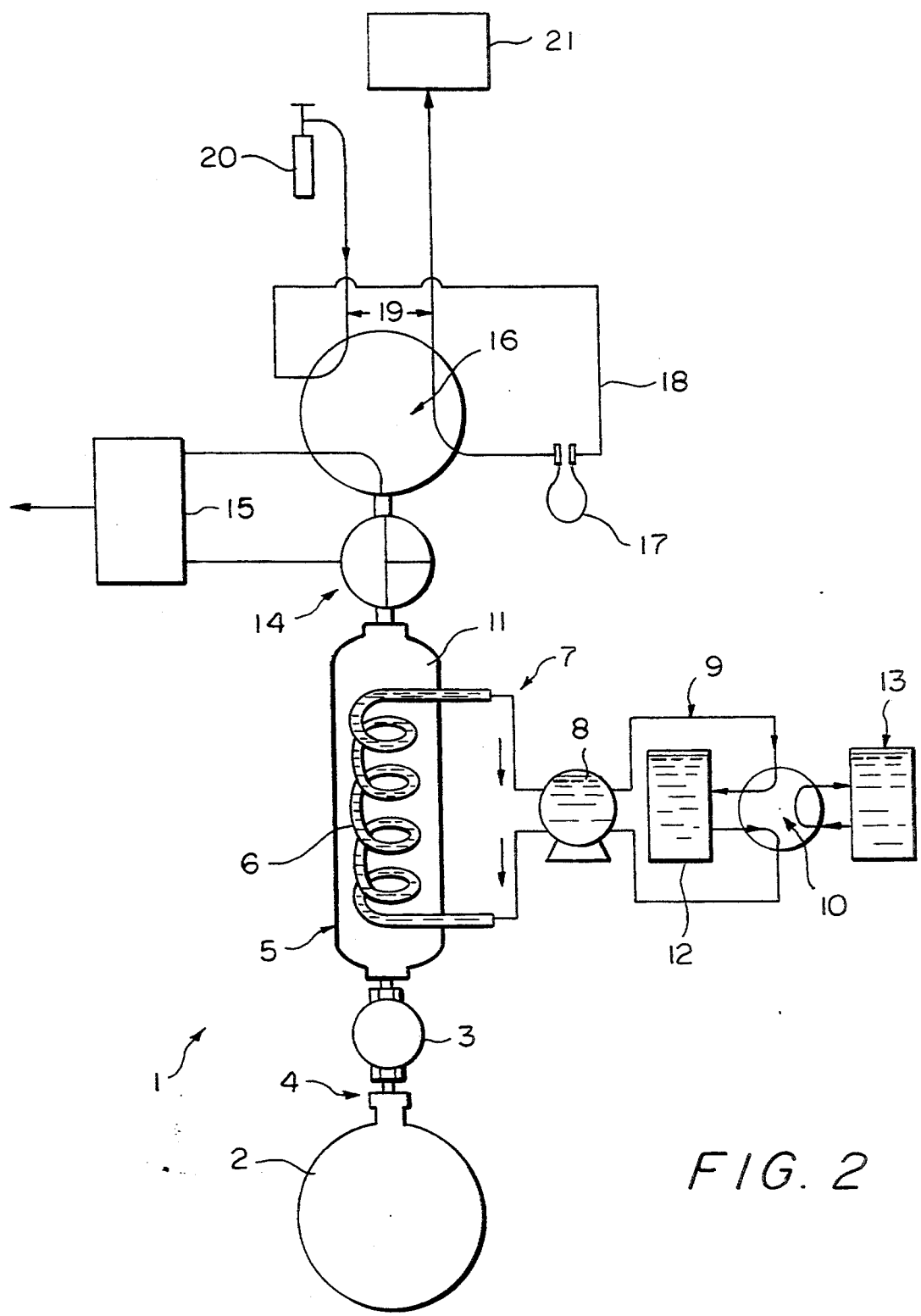
FIG. 2 is a schematic elevational view of the novel apparatus of the invention in the injection position and the condenser fluid is adjusted to a heating means.

When sufficient distillate or effluent has been collected in the cryotrap 17, the sampling valve 16 or series of valves performing the same function are changed so that no further gasses from the sample can enter the cryotrap. Substantially simultaneously, the vacuum line connected to loop 18 is disconnected and an inert gas 20 is passed through the cryotrap 17 to revolatilize the compounds and transport them to a suitable detection means. The results of these changes are shown in FIG. 2 which constitutes the injection position. The positioning of the vacuum pump valve 14 may be in any position during the injection position. Likewise the sample chamber valve 3 may be closed during the injection position and while injecting and/or cleaning the condenser, the bulb 2 may be removed and replaced with a different sample. Automated variations on these changes may also be used.

One very suitable inert gas is helium which not only is chemically inert but is very characteristic in and does not interfere with the analysis by GC/MS. The detector 21 may be any of the well known systems for detecting the compounds of interest. The choice of detector or combination of detectors in series or parallel and its components will vary with the compound being detected. A gas chromatograph, particularly when used with a mass spectrometer has been found to be advantageous.

The advantages of the method and apparatus of the present invention includes the ability to continuously run sample after sample without cleaning the entire system of residue each time. This makes the present system much easier to decontaminate than those used previously. The condenser 5 also permits separation of water or other common interferants. Azeotropes may constitute the first portion of condensed material. Very volatile azeotropes may be co-isolated in the cryotrap 17 with the volatile organic compounds.

The condensed azeotrope or other condensate may be collected from the condenser and separately analyzed. One simple way of doing this is to close the sample chamber valve 3 once the azeotrope has been condensed in the condenser 5. The temperature in the condenser is then raised and/or the vacuum pressure lowered to revolatilize the azeotrope which is then trapped in the cryotrap 17 and then or later analyzed. Alternatively, the azeotrope or condensate may be drained from the condenser and separately analyzed.

In a similar fashion, different fractions of condensed material may be analyzed. For example, napthalenes may primarily condense with a fraction containing water. Before attempting to volatilize or revolatilize the condensed material from a cryotrap, compounds previously trapped should be flushed from the cryotrap to prevent cross contamination. Azeotrope fraction, condensate or residue in the sample chamber may alternatively be collected and analyzed separately in a different system using any other known analytical chemistry technique such as high performance liquid chromatography (HPLC), supercritical fluid extraction (SCFE) etc..

Representative fractions include the most volatile fraction (boiling point less than about 200° C.) assayed as described above. A second fraction may be an azeotrope fraction. A third fraction may be the condenser coil condensate with boiling points up to 300° C. A fourth fraction is the sample residue or solvent extract from the sample residue. Differing fractions may be produced as desired depending on the sample constitution and the choice of analysis techniques. For example, if one were to assay for lead or cadmium, the non-volatilized residue would most likely contain these metals and it would be appropriate to measure the sample using atomic adsorption spectroscopy.

A particular advantage to the present system is that it is inert to the chemical composition of the sample. Unlike other previously used systems, no heat is present to degrade chemicals or promote reactions which produce additional compounds not previously present in the sample. This is particularly important when analyzing a sample for contamination as neither a false positive or a false negative is tolerable. Additionally, the temperature at which the system is run during the distillation phase is reasonably close to ambient temperature for the sample; thus, not altering the sample for further analysis by a different system.

EXAMPLE 1: STANDARDS PREPARATION

Stock solutions for standards were prepared in methanol as follows. 9.8 ml of methanol is placed in a 10 ml tared ground glass stoppered volumetric flask. The flask is allowed to stand unstoppered for about ten minutes or until all alcohol wetted surfaces have dried. The flask is weighed to the nearest 0.1 mg.

To prepare solutions of liquid compounds, a 100 µm syringe filed with the compound is used to introduce two or more of drops into the flask. The liquid must fall directly into the alcohol without contacting the neck of the flask. The flask is reweighed to determine the amount of added compound.

To prepare standard solutions of gaseous compounds, such as those boiling below 30° C., a 5 ml gas tight valved syringe filled with the standard is used. The syringe needle is lowered to 5 mm above the surface of the methanol. The reference standard is slowly introduced above the surface of the liquid. The heavy gas rapidly dissolves in the methanol. Standards may also be prepared by using a lecture bottle equipped with a Hamilton Lecture Bottle Septum. A Teflon tube is attached to the side-arm relief valve and a gentle stream of gas is directed onto the methanol surface.

For either procedure, the flask is reweighed, diluted to volume, stoppered and mixed by inverting the flask several times. The concentration in Micrograms/microliter is calculated from the net gain in weight. When the compound standard is assayed to be 96% or greater, the weight may be used without correction to calculate the concentration of the stock solution. Commercially prepared stock solutions may alternatively be used.

Stock solutions are transferred to Teflon-sealed screw cap bottles and stored with minimal headspace at $-10°$ to $-20°$ C. away from light. Many standards will be acceptable for up to six months. Standards of gaseous compounds should be prepared fresh every two months. Reactive compounds such as 2-chloroethylvinyl ether and styrene may need to be prepared more frequently. Stock solutions may need to be diluted to prepare secondary dilution standards in the appropriate concentrations which must be stored similarly or prepared shortly before use.

Surrogate standards are prepared-in the same manner as above. Toluene-d8, 4-bromofluorobenzene and 1,2-dichloroethaned4 are suitable examples. The surrogate standards may be used to spike samples to be assayed. A stock concentration of 25 µg/ml methanol is appropriate with each 5 ml sample being spiked with 10 µl of this solution prior to analysis.

Internal standards are also prepared in the same manner as above. Bromochloromethane, 1,4-difluorobenzene and chlorobenzene-d5 are among the possible choices. Others may be used provided that they have retention times similar to the compounds being detected by GC/MS. The same concentrations as surrogate standards may be used. 4-Bromofluorobenzene (BFB) standards should be prepared at 25 ng/µl.

Standards are made at five or greater concentration levels to prepare a standard plot. Ideally multiple standards should be both greater and lesser than the suspected sample concentration and should be within the working range of the GC/MS system being used. Reagent grade or purge and trap grade water or methanol should be used for dilution.

Standards used to spike samples should be prepared in the same manner and the choice of compound to spike a sample should be based upon the compound one wishes to assay. The spiking standard should behave in a similar manner in the GC/MS.

All solvents should be of a very high grade. Water should be passed through an activated carbon filter, or boiled to remove trace organic compounds. The water should be stored promptly in a tightly closed and sealed container to prevent contamination with ambient gases. Methanol should be pure and stored separately from other solvents.

EXAMPLE 2: APPARATUS

The apparatus displayed in FIGS. 1 and 2 includes a 100 ml Pyrex bulb sample chamber joined to a 15 mm I.D. Pyrex O-ring connector. The bulb is capable of accepting an internal pressure of 0.1 Torr without implosion. The bulb is then sealed for sample storage with a Buna-N O-ring, a 15 mm i.d. O-ring connector cap and a pinch clamp. This is connected to a sample chamber valve, as for example a stopcock, which in turn is connected to the bottom of a condenser. The condenser is thermoregulated by coils through which a fluid such as isopropyl alcohol or salt water is pumped. The condenser fluid flow is driven with a peristaltic pump and through a six port valve to either a hot bath or cold bath to regulate temperature.

At the top of the condenser, a three way valve such as a T-valve is placed to direct flow to either a vacuum pump, a sampling valve, both or neither.

The sampling valve used in the this example is a six port valve attached to six conduits where in the loading position as shown in FIG. 1, the gas from the condenser which passes through the vacuum pump valve flows through the six port valve through a conduit to-a cryotrap maintained at liquid nitrogen temperatures. From the cryotrap, a conduit connects to the six port valve and out another conduit to the vacuum pump. Through the other two ports of the six port valve, helium is passed in and out of the valve to a gas chromatograph/mass spectrometer.

When the six port valve is adjusted to be in the injection position, as shown in FIG. 2, the gasses from the condenser and vacuum pump valve are directed to the vacuum pump. The helium is directed through the valve and to the cryotrap in the reverse direction as gas flow previously. From the cryotrap, gas flows through the sampling valve to a GC/MS.

The Gas chromatograph column is 30 meters long by 0.7 mm I.D. DB-624 with 3.0 micron film thickness. The mass spectrometer is capable of scanning from 35-350 amu every two seconds or less using a nominal 70 volts electron energy in the electron impact mode and detecting the sample when 50 ng of 4-bromofluorobenzene in injected in to the gas chromatograph inlet. The interface between GC and MS is a heated glass jet separator capable of being heated from 100°-220° C. and removing 10-40 ml/min. of helium from the exit of the GC.

EXAMPLE 3: OPERATION

The cryotrap is placed in liquid nitrogen which is replaced as needed throughout the operation. The sample valve is placed in the load position. Samples are placed in the sample chamber and the chamber attached to the apparatus. The coolant/heat valve is adjusted so that the condenser fluid is circulating and at the desired temperature. The vacuum pump is turned on and the vacuum pump valve and sample chamber valve are opened to begin distillation/purging. After five minutes the pressure at the vacuum pump, as measured by a Pirani gauge reads about 0.1 Torr and a Pirani gauge reads less than about 250 Torr at the sample chamber. Distillation continues for another five minutes to complete distillation at which time the sample chamber pressure should be approximately 10 Torr.

Once distillation is complete, the sampling valve is adjusted to the injection position. The liquid nitrogen is removed from the cryotrap and replaced with a beaker of hot (about 90° C.) tap water. The GC/MS then begins to collect data. At this stage, the sample chamber may be removed and the apparatus prepared for another sample. If multiple samples are connected, a new sample chamber may be connected in sequence.

The apparatus may be prepared for another sample by closing the sample chamber valve, removing the sample chamber and adjusting the circulating fluid in the condenser to at least 45° C. and open the condenser to the vacuum pump for at least about ten minutes to volatilize and remove any remaining compounds. This process may be performed while the six port valve is in the injection position and the cryotrap, loop and other conduits are being evacuated or purged with helium.

The condensate, various fractions and sample residue may also be collected for analyses analyzed to measure additional compounds by the same or different techniques.

RESULTS

The compounds listed in Table 1 were assayed in the above system and methods using standard stock solutions of analyte. Using a 30 meter, 0.53 mm bore, stable wax, 1 micron film thickness column for the GC column, the retention times in the GC column and the detectable ions in the Mass spectrometer for each are given in Table 1. The GC temperature program involved three minutes at 10° C. and thereafter increased to 270° C. at a rate of 5° C. per minute. The final temperature, 270° C., was held for three minutes.

Spiked water and spiked soil samples were tested for the efficiency at which certain compounds are distilled and recovered in the cryotrap. Concentrations were 50 ppb and the sample was distilled for ten minutes at a condenser temperature of −15° C. The GC column was a 30 meter, 0.53 mm bore with 1 micron stabilized wax. The results are shown in Table 2.

Recovery percentages from spiked-water and cod liver oil/water emulsion for various analytes are given in Table 3. Recovery percentages from spiked cod liver oil for various analytes are given in Table 4. Likewise for spiked soil which is dry, wet, oily, or wet and oily which are presented in Table 5. The recovery rate is quite high, and is not as adversely affected by the sample matrix, unlike the recovery rates reported in the previous publications and patents.

The detection limits data presented in Table 6 and Table 7 refers to the amount one needs to have a 95% chance of being measured compared to the standards. This does not actually imply that this is the lowest level of detection which is more closely related to sample size and detector selection.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

TABLE 1

RETENTION TIMES AND GC/MS CHARACTERISTIC IONS FOR VOLATILE ANALYTES

| Analytes | Retention Time (min.) | Primary Ion | Secondary Ion(s) |
|---|---|---|---|
| Acetone | 4.13 | 43 | 58 |
| Acrolein | 3.02 | 56 | 55, 58 |
| Acrylonitrile | 3.68 | 53 | 52, 51 |
| Benzene | 7.98 | 78 | 52, 77 |
| Bromochloromethane (I.S.) | 9.3 | 128 | 49, 130, 51 |
| Bromodichloromethane | 14.3 | 83 | 85, 129 |
| 4-Bromofluorobenzene (surr.) | 28.3 | 95 | 174, 176 |
| Bromoform | 19.8 | 173 | 171, 175, 252 |
| 2-Butanone | 17.49 | 72 | 57, 43 |
| Carbon disulfide | 3.11 | 76 | 78 |
| Carbon tetrachloride | 13.7 | 117 | 119, 121 |
| Chlorobenzene | 24.6 | 112 | 114, 77 |
| Chlorobenzene-d5 (I.S.) | 15.35 | 117 | 82, 119 |
| Chlorodibromomethane | 14.12 | 129 | 208, 206 |
| Chloroethane | 4.6 | 64 | 66, 49 |
| 2-Chloroethyl vinyl ether | 18.6 | 63 | 65, 106 |
| Chloroform | 11.4 | 83 | 85, 47 |
| Chloromethane | 2.3 | 50 | 52, 49 |
| Dibromomethane | NA | 93 | 174, 95 |
| 1,4-Dichloro-2-butane | NA | 75 | 53, 89 |
| Dichlorodifluoromethane | NA | 85 | 87, 50, 101 |
| 1,1-Dichloroethane | 5.13 | 63 | 65, 83 |

TABLE 1-continued

RETENTION TIMES AND GC/MS CHARACTERISTIC IONS FOR VOLATILE ANALYTES

| Analytes | Retention Time (min.) | Primary Ion | Secondary Ion(s) |
|---|---|---|---|
| 1,2-Dichloroethane | 10.1 | 62 | 64, 98 |
| 1,2-Dichloroethane-d4 (surr.) | 12.1 | 65 | 102 |
| 1,1-Dichloroethene | 9.0 | 96 | 61, 98 |
| trans-1,2-Dichloroethene | 10.0 | 96 | 61, 98 |
| 1,2-Dichloropropane | 15.7 | 63 | 62, 41 |
| cis-1,3-Dichloropropene | 15.9 | 75 | 77, 39 |
| trans-1,3-Dichloropropene | 17.2 | 75 | 77, 39 |
| 1,4-Difluorobenzene (I.S.) | 19.6 | 114 | 63, 88 |
| Ethanol | 4.95 | 31 | 45, 27, 46 |
| Ethylbenzene | 26.4 | 106 | 91 |
| Ethyl methacrylate | 13.38 | 69 | 41, 39, 99 |
| 2-Hexanone | 12.36 | 43 | 58, 57, 100 |
| Iodomethane | NA | 142 | 127, 141 |
| Methylene chloride | 6.4 | 84 | 49, 51, 86 |
| 4-Methyl-2-pentanone | 12.16 | 43 | 58, 100 |
| Styrene | 17.16 | 104 | 78, 103 |
| 1,1,2,2-Tetrachloroethane | 22.1 | 83 | 85, 131, 133 |
| Tetrachloroethene | 22.2 | 164 | 129, 131, 166 |
| Toluene | 23.5 | 92 | 91, 65 |
| Toluene-d8 (surr.) | 12.03 | 98 | 70, 100 |
| 1,1,1-Trichloroethane | 13.4 | 97 | 99, 117 |
| 1,1,2-Trichloroethane | 17.2 | 97 | 83, 85, 99 |
| Trichloroethene | 16.5 | 130 | 95, 97, 132 |
| Trichlorofluoromethane | 8.3 | 101 | 103, 66 |
| 1,2,3-Trichloropropane | NA | 75 | 110, 77, 61 |
| Vinyl acetate | 5.68 | 43 | 86 |
| Vinyl chloride | 3.8 | 62 | 64, 61 |
| m-Xylene | 17.06 | 106 | 91 |
| p-Xylene | 17.33 | 106 | 91 |
| o-Xylene | 16.39 | 106 | 91 |

GC Column: 30 meter Stabilized Wax. 1 Micron film thickness. 0.53 mm bore.
GC Program: Three minutes at 10° C. Temperature raised from 10° C. to 270° C. at 5° C./min. 270° C. held for three minutes.

TABLE 2

| | Vacuum Distillation Analytes[a] | | | | | | | |
|---|---|---|---|---|---|---|---|---|
| COMPOUNDS | MOL WT | BP °C. | MP °C. | SOLUBIL. IN H2O (PPM) | 5 ML WATER RECOVERY/ PRECISION | | 5 G SOIL[b] RECOVERY/ PRECISION | |
| Diethyl ether | 74.1 | 35 | −116 | 60400 | 77.5% | 3.6% | 83.2% | 19.0% |
| Allyl chloride | 76.5 | 45 | −135 | 3600 | 85.9% | 3.2% | 81.0% | 18.4% |
| Acetonitrile | 41.1 | 82 | −44 | 1000000 | 68.0% | 2.8% | 76.9% | 9.4% |
| Acrylonitrile | 53.1 | 77 | −84 | 73000 | 30.3% | 21.7% | 61.8% | 6.9% |
| Methy acrylonitrile | 67.9 | 90 | −36 | 26000 | 64.2% | 6.3% | 74.7% | 16.0% |
| Propionitrile | 55.1 | 97 | −93 | 100000 | 19.0% | 13.9% | 49.7% | 10.9% |
| Isobutanol | 74.1 | 108 | −108 | 100000 | 12.2% | 4.6% | 21.0% | 5.6% |
| 1,4-Dioxane | 88.1 | 101 | 12 | 1000000 | 15.6% | 5.2% | 24.3% | 9.8% |
| Methyl methacrylate | 100.1 | 100 | −48 | 16000 | 50.6% | 4.8% | 72.6% | 20.9% |
| Pyridine | 79.1 | 115 | −42 | 1000000 | 8.9% | 11.2% | 9.4% | 6.0% |
| Ethyl methacrylate | 114.1 | 118 | | | 39.7% | 5.4% | 50.7% | 5.1% |
| n-Nitrosodimethylamine | 74.8 | 151 | 61 | 1000000 | 2.6% | 3.7% | 7.3% | 2.0% |
| Dibromomethane | 173.9 | 97 | −53 | 11500 | 50.5% | 5.5% | 75.2% | 12.3% |
| 2-Picoline | 93.1 | 128 | −67 | 1000000 | 11.7% | 9.5% | 4.1% | 4.0% |
| n-Nitrosodimethylethylamine | | | | | 6.0% | 3.4% | 6.3% | 1.6% |
| iso-Propylbenzene | 120.2 | 152 | −96 | 5000 | 64.1% | 1.3% | 72.8% | 11.8% |
| 2-Fluorophenol | 112.1 | 172 | 16 | N/A | 5.4% | 3.9% | 8.2% | 4.1% |
| Bromobenzene | 157.0 | 156 | −31 | 400 | 56.6% | 2.3% | 77.2% | 12.8% |
| n-Propylbenzene | 120.2 | 159 | −99 | 60 | 58.6% | 2.1% | 72.0% | 8.1% |
| n-Nitroso-di-n-ethylamine | 102.1 | | | | 5.6% | 2.8% | 7.3% | 1.9% |
| 4-Chlorotoluene | 126.6 | 162 | 7 | 5 | 56.6% | 2.7% | 73.5% | 9.1% |
| 1,3,5-Trimethyl benzene | 120.2 | 165 | −45 | 2000 | 57.3% | 1.5% | 72.1% | 7.2% |
| tert-Butylbenzene | 134.2 | 169 | −58 | 290 | 55.5% | 2.3% | 70.6% | 7.8% |
| 1,2,4-Trimethyl benzene | 120.2 | 169 | −44 | 1 | 55.8% | 2.8% | 70.6% | 7.0% |
| sec-butylbenzene | 134.2 | 173 | −83 | 320 | 56.2% | 2.7% | 70.5% | 7.3% |
| 1,3-Dichlorobenzene | 147.0 | 173 | −25 | 11000 | 54.1% | 2.3% | 69.4% | 8.0% |
| bis(2-Chloroethyl) ether | 143.0 | 179 | −52 | 1 | 10.6% | 1.5% | 19.5% | 1.5% |
| 1,3-Dichlorobenzene | 147.0 | 174 | 53 | 10000 | 53.3% | 2.2% | 70.4% | 8.2% |

TABLE 2-continued

| | | | | Vacuum Distillation Analytes[a] | | | | |
|---|---|---|---|---|---|---|---|---|
| COMPOUNDS | MOL WT | BP °C. | MP °C. | SOLUBIL. IN H2O (PPM) | 5 ML WATER RECOVERY/ PRECISION | | 5 G SOIL[b] RECOVERY/ PRECISION | |
| Aniline | 93.1 | 184 | −6 | 32500 | 17.2% | 12.2% | 9.2% | 8.1% |
| para-iso-Propyl toluene | 134.2 | 177 | −68 | 1 | 56.6% | 3.1% | 63.8% | 5.6% |
| 2-Chlorophenol | 128.6 | 175 | 9 | 5 | 6.9% | 4.5% | 5.6% | 4.0% |
| 1,2-Dichlorobenzene | 147.0 | 180 | −17 | 10000 | 52.1% | 3.2% | 66.7% | 7.9% |
| n-Butylbenzene | 134.2 | 183 | −89 | 5000 | 55.0% | 2.2% | 59.2% | 5.0% |
| Phenol | 94.1 | 182 | 41 | 70000 | 6.2% | 5.9% | 4.6% | 3.9% |
| Benzyl alcohol | 108.1 | 205 | −15 | 80000 | 4.2% | 5.9% | 5.6% | 6.4% |
| Acetophenone | 120.2 | 202 | 20 | 5500 | 6.2% | 3.0% | 8.3% | 1.5% |
| o-Toluidine | 107.2 | 200 | −16 | 17000 | 4.0% | 3.8% | 4.8% | 3.8% |
| n-Nitroso-di-n-propylamine | 130.1 | 78 | | 5 | 4.4% | 2.3% | 5.6% | 1.7% |
| n-Nitrosomorpholine | 116.1 | 139 | 29 | 1000000 | 4.2% | 4.0% | 3.5% | 1.6% |
| 2-Methylphenol | 108.1 | 191 | 30 | 775000 | 3.0% | 3.2% | 2.6% | 2.1% |
| n-Nitroso-pyrrolidine | 100.1 | 105 | | 1000000 | 3.2% | 3.7% | 3.4% | 2.4% |
| n-Nitroso-piperidine | 114.1 | 217 | | 1000000 | 4.5% | 4.0% | 4.1% | 2.8% |
| 1,2,4-Trichloro-benzene | 181.5 | 221 | 53 | 1 | 29.3% | 2.2% | 32.5% | 2.3% |
| bis-2-Chloroethoxy methane | N/A | N/A | N/A | N/A | 4.3% | 2.8% | 3.7% | 3.7% |
| Naphthalene | 128.2 | 217 | 80 | 3400 | 18.9% | 2.2% | 22.7% | 2.9% |
| 2,4-Dimethylphenol | 122.2 | 210 | 27 | 5 | 1.7% | 2.2% | 7.5% | 4.5% |
| 1,2,3-Trichloro benzene | 181.5 | 221 | 53 | 1 | 21.8% | 3.1% | 25.6% | 2.6% |
| 4-Chloroaniline | 127.6 | 121 | 73 | 5 | 5.0% | 6.9% | 15.4% | 17.4% |
| 2-Methyl-naphthalene | 142.2 | 241 | 35 | 1 | 8.7% | 2.1% | 15.9% | 1.5% |
| n-Nitroso-di-n-butylamine | 158.2 | 105 | | | 1.4% | 1.2% | 8.3% | 7.4% |
| 4-Chloro-3-methyl phenol | 142.6 | 235 | 68 | 1 | 5.4% | 7.5% | 14.2% | 13.3% |
| 2-Nitroaniline | 138.1 | 284 | 69 | 5 | 6.7% | 9.4% | 4.4% | 4.6% |
| Pentachlorobenzene | 250.3 | 275 | 82 | 1 | 4.6% | 1.0% | 17.1% | 7.2% |
| Dibenzofuran | 168.2 | 285 | 82 | 1 | 3.1% | 1.7% | 15.9% | 9.3% |

[a]Sample distillation results are for 10 minute distillation times, and condenser temperature held at −15° C. A 30 meter 1 micron stabilized wax 0.53 mm bore column was used for chromatography. Sample concentration were 50 ppb.
[b]One ml of water was added to soil.

TABLE 3

| PRECISION AND ACCURACY FOR VOLATILE ORGANIC ANALYTES[a] | | | | |
|---|---|---|---|---|
| Analytes | Water 5 mL | Water 20 mL | H2O/Oil[b] 5 mL | H2O/Oil[c] 20 mL |
| 1. Chloromethane | 93 ± 18[d] | 98 ± 13 | 177 ± 43 | 126 ± 41 |
| 2. Bromomethane | 105 ± 9 | 99 ± 21 | 120 ± 20 | 90 ± 23 |
| 3. Vinyl Chloride | 105 ± 9 | 98 ± 19 | 118 ± 28 | 87 ± 27 |
| 4. Chloroethane | 88 ± 10 | 81 ± 17 | 102 ± 16 | 76 ± 20 |
| 5. Methylene Chloride | 72 ± 13 | 87 ± 10 | 111 ± 20 | 111 ± 30 |
| 6. Acetone | 70 ± 23 | 60 ± 41 | 95 ± 35 | 87 ± 42 |
| 7. Carbon Disulfide | 110 ± 8 | 109 ± 30 | 115 ± 20 | 95 ± 29 |
| 8. 1,1-Dichloroethene | 84 ± 6 | 74 ± 15 | 103 ± 17 | 70 ± 16 |
| 9. 1,1-Dichloroethane | 96 ± 11 | 98 ± 14 | 108 ± 18 | 84 ± 12 |
| 10. trans-1,2-Dichloroethene | 84 ± 6 | 88 ± 11 | 103 ± 17 | 70 ± 16 |
| 11. Cis-1,2-Dichloroethene | 85 ± 8 | 82 ± 18 | 86 ± 11 | 74 ± 12 |
| 12. Chloroform | 94 ± 14 | 86 ± 16 | 75 ± 12 | 70 ± 9 |
| 13. 1,2-Dichloroethane | 93 ± 15 | 90 ± 14 | 85 ± 16 | 74 ± 6 |
| 14. 2-Butanone[e] | 79 ± 45 | 88 ± 13 | 47 ± 15 | N/A |
| 15. 1,1,1-Trichloroethane | 96 ± 13 | 90 ± 15 | 81 ± 14 | 73 ± 9 |
| 16. Carbon Tetrachloride | 91 ± 14 | 90 ± 18 | 72 ± 17 | 64 ± 12 |
| 17. Vinyl Acetate | 72 ± 13 | 82 ± 22 | 87 ± 21 | 74 ± 11 |
| 18. Bromodichloromethane | 92 ± 11 | 91 ± 17 | 66 ± 12 | 58 ± 17 |
| 19. 1,1,2,2-Tetrachloroethane | 78 ± 20 | 72 ± 20 | 34 ± 17 | 28 ± 7 |
| 20. 1,2-Dichloropropane | 89 ± 14 | 86 ± 18 | 67 ± 11 | 58 ± 16 |
| 21. trans-1,3-Dichloropropene NA | 94 ± 15 | 87 ± 18 | 54 ± 9 | 53 ± 9 |
| 22. Trichloroethene | 86 ± 8 | 82 ± 18 | 61 ± 9 | 62 ± 9 |
| 23. Dibromochloromethane | 90 ± 12 | 87 ± 20 | 47 ± 9 | 50 ± 10 |
| 24. 1,1,2-Trichloroethane | 87 ± 14 | 83 ± 20 | 51 ± 8 | 81 ± 22 |
| 25. Benzene | 86 ± 9 | 83 ± 15 | 80 ± 12 | 68 ± 10 |
| 26. cis-1,3-Dichloropropene | 94 ± 12 | 87 ± 19 | 61 ± 9 | 57 ± 12 |
| 27. Bromoform | 85 ± 19 | 83 ± 23 | 35 ± 8 | 34 ± 7 |
| 28. 2-Hexanone | 54 ± 17 | 56 ± 24 | 66 ± 8 | 42 ± 7 |
| 29. 4-Methyl-2-pentanone | 69 ± 20 | 54 ± 22 | 43 ± 7 | 29 ± 6 |
| 30. Tetrachloroethene | 91 ± 11 | 85 ± 19 | 47 ± 11 | 46 ± 8 |
| 31. Toluene | 89 ± 11 | 81 ± 24 | 51 ± 10 | 50 ± 9 |

TABLE 3-continued

PRECISION AND ACCURACY FOR VOLATILE ORGANIC ANALYTES[a]

| Analytes | Water 5 mL | Water 20 mL | H2O/Oil[b] 5 mL | H2O/Oil[c] 20 mL |
|---|---|---|---|---|
| 32. Chlorobenzene | 88 ± 12 | 86 ± 21 | 40 ± 9 | 43 ± 10 |
| 33. Ethyl Benzene | 90 ± 12 | 80 ± 18 | 40 ± 10 | 45 ± 9 |
| 34. Styrene | 89 ± 9 | 85 ± 21 | 34 ± 9 | 35 ± 7 |
| 35. Para Xylene | 86 ± 8 | 82 ± 19 | 38 ± 10 | 43 ± 12 |
| 36. Ortho Xylene | 86 ± 10 | 83 ± 19 | 34 ± 9 | 42 ± 10 |
| Surrogates | | | | |
| Bromochloromethane | 82 ± 12 | 83 ± 19 | 79 ± 10 | N/A |
| 1,4-Difluorobenzene | 89 ± 11 | 83 ± 17 | 65 ± 10 | N/A |
| Chlorobenzene-d5 | 90 ± 11 | 88 ± 20 | 41 ± 10 | N/A |
| 1,4-dichlorobenzene | 109 ± 19 | 97 ± 20 | 29 ± 9 | N/A |
| 1,2-dichloroehane | 94 ± 15 | 94 ± 12 | 91 ± 17 | 78 ± 8 |
| Toluene-d8 | 93 ± 11 | 85 ± 18 | 52 ± 9 | 54 ± 8 |
| Bromofluorobenzene | 94 ± 11 | 88 ± 22 | 33 ± 8 | 32 ± 6 |

[a]Results are for 10 min. distillation times, and condenser temperature held at −10° C.. Five to six replicates were run and recoveries are relative to the internal standard d3-Vinylchloride using GC/MS. A 30 meter, 1 micron stabilized wax 0.53 mm bore column was used for chromatography. Standards were replicated two to three times.
[b]Sample contained 1 gram cod liver oil and 5 ml water. An emulsion was created by adding 0.2 ml of water saturated with lecithin.
[c]Sample contained 1 g cod liver oil and 20 ml water. An emulsion was created by adding 0.2 ml of water saturated with lecithin.
[d]One sigma error resulting from the propagation of replicate standard and replicate sample measurement errors.
[e]Column used in this study did not resolve 2-butane effectively. There were interfering compounds in the oil matrix used that co-diluted with 2-butanone and complicated integration.

TABLE 4

PRECISION AND ACCURACY FOR VOLATILE ORGANIC ANALYTES[a]

| Analytes | Oil Recovery[b] |
|---|---|
| 1. Chloromethane | 182 ± 97 |
| 2. Bromomethane | 87 ± 15 |
| 3. Vinyl Chloride | 81 ± 12 |
| 4. Chloroethane | 72 ± 21 |
| 5. Methylene Chloride | NA[c] |
| 6. Acetone | NA |
| 7. Carbon Disulfide | 92 ± 14 |
| 8. 1,1-Dichloroethene | 71 ± 24 |
| 9. 1,1-Dichloroethane | 93 ± 8 |
| 10. trans-1,2-Trichloroethane | 79 ± 14 |
| 11. Cis-1,2-Dichloroethene | 71 ± 24 |
| 12. Chloroform | 60 ± 7 |
| 13. 1,2-Dichloroethane | 65 ± 3 |
| 14. 2-Butanone | 128 ± 21.5[d] |
| 15. 1,1,1-Trichloroethane | 88 ± 40 |
| 16. Carbon Tetrachloride | 54 ± 5 |
| 17. Vinyl Acetate | 114 ± 33 |
| 18. Bromodichloromethane | 41 ± 5 |
| 19. 1,1,2,2-Tetrachloroethane | 25 ± 10 |
| 20. 1,2 Dichloropropane | 47 ± 11 |
| 21. trans-1,3-Dichloropropene NA | 34 ± 5 |
| 22. Trichloroethene | 50 ± 7 |
| 23. Dibromochloromethane | 25 ± 6 |
| 24. 1,1,2-trichloroethane | 29 ± 7 |
| 25. Benzene | 81 ± 12 |
| 26. Cis-1,3-Dichloropropene | 42 ± 6 |
| 27. Bromoform | 19 ± 7 |
| 28. 2-Hexanone | 67 ± 9 |
| 29. 4-Methyl-2-pentanone | 100 ± 33 |
| 30. Tetrachlorethene | 30 ± 5 |
| 31. Toluene | 48 ± 9 |
| 32. Chlorobenzene | 24 ± 4 |
| 33. Ethylbenzene | 31 ± 2 |
| 34. Styrene | 21 ± 4 |
| 35. Para-xylene | 25 ± 3 |
| 36. Ortho-xylene | 45 ± 19 |
| Surrogates | |
| Bromochloromethane | 61 ± 8 |
| 1,4-Difluorobenzene | 49 ± 5 |
| Chlorobenzene-d5 | 24 ± 4 |
| 1,2-dichloroethane | 65 ± 3 |
| Toluene-d8 | 41 ± 5 |

TABLE 4-continued

PRECISION AND ACCURACY FOR VOLATILE ORGANIC ANALYTES[a]

| Analytes | Oil Recovery[b] |
|---|---|
| Bromofluorobenzene | 20 ± 5 |

[a]Results are for 10 min. distillations times, and condenser temperature held at −10° C. A 30 meter, 1 micron stabilized wax 0.53 mm bore column was used for chromatography.
[b]Analyte recoveries from 1 gram cod liver oil. Each analyte was spiked to 25, 50 and 200 ppb concentrations and the results reflect composite recoveries.
[c]Not available. Laboratory contamination of sample by those analytes prevented assessment.
[d]200 ppb spike recovery only.

TABLE 5

PRECISION AND ACCURACY FOR VOLATILE ORGANIC ANALYTES IN SOIL[a]

| Analytes | Soil/Water[b] | Soil/Oil[c] | Soil/Oil Water[d] |
|---|---|---|---|
| 1. Chloromethane | 66 ± 32 | 66 ± 32 | 119 ± 84 |
| 2. Bromomethane | 63 ± 33 | 81 ± 24 | 82 ± 23 |
| 3. Vinyl Chloride | 60 ± 25 | 79 ± 23 | 79 ± 30 |
| 4. Chloroethane | 48 ± 20 | 70 ± 14 | 58 ± 22 |
| 5. Methylene Chloride | 66 ± 15 | 114 ± 12 | 84 ± 5 |
| 6. Acetone | Int[e] | Int | 50 ± 13 |
| 7. Carbon Disulfide | 50 ± 20 | 92 ± 19 | 53 ± 11 |
| 8. 1,1-Dichloroethene | 53 ± 20 | 81 ± 12 | 65 ± 9 |
| 9. 1,1-Dichloroethane | 67 ± 19 | 101 ± 21 | 68 ± 4 |
| 10. trans-1,2-Trichloroethane | 59 ± 19 | 105 ± 14 | 63 ± 5 |
| 11. Cis-1,2-Dichloroethene | 66 ± 14 | 126 ± 13 | 69 ± 11 |
| 12. Chloroform | 114 ± 28 | INT | 126 ± 4 |
| 13. 1,2-Dichloroethane | 75 ± 25 | 91 ± 16 | 73 ± 4 |
| 14. 2-Butanone | Int | 60 ± 63 | Int |
| 15. 1,1,1-Trichloroethane | 137 ± 23 | INT | INT |
| 16. Carbon Tetrachloride | 88 ± 59 | INT | INT |
| 17. Vinyl Acetate | 83 ± 12 | Int | Int |
| 18. Bromodichloromethane | 49 ± 12 | 69 ± 25 | 50 ± 4 |
| 19. 1,1,2,2-Tetrachloroethane | 75 ± 22 | 26 ± 9 | 35 ± 5 |
| 20. 1,2 Dichloropropane | 56 ± 17 | 79 ± 14 | 53 ± 9 |
| 21. trans-1,3-Dichloropropene | 70 ± 18 | 66 ± 18 | 51 ± 5 |
| 22. Trichloroethene | 52 ± 16 | 76 ± 16 | 48 ± 7 |
| 23. Dibromochloromethane | 74 ± 18 | 65 ± 22 | 47 ± 4 |
| 24. 1,1,2-trichloroethane | 66 ± 20 | 56 ± 17 | 47 ± 6 |
| 25. Benzene | 54 ± 12 | Cont[f] | 83 ± 5 |
| 26. Cis-1,3-Dichloropropene | 64 ± 20 | 73 ± 17 | 53 ± 5 |
| 27. Bromoform | 81 ± 21 | 30 ± 14 | 34 ± 3 |
| 28. 2-Hexanone | 99 ± 20 | 82 ± 19 | 57 ± 5 |

TABLE 5-continued

PRECISION AND ACCURACY FOR VOLATILE ORGANIC ANALYTES IN SOIL[a]

| Analytes | Soil/Water[b] | Soil/Oil[c] | Soil/Oil Water[d] |
|---|---|---|---|
| 29. 4-Methyl-2-pentanone | 79 ± 24 | 143 ± 28 | 81 ± 12 |
| 30. Tetrachlorethene | 56 ± 16 | 62 ± 17 | 43 ± 6 |
| 31. Toluene | 50 ± 13 | Cont | Cont |
| 32. Chlorobenzene | 61 ± 18 | 47 ± 17 | 38 ± 4 |
| 33. Ethylbenzene | 70 ± 23 | 83 ± 23 | 56 ± 5 |
| 34. Styrene | 66 ± 19 | 39 ± 16 | 32 ± 4 |
| 35. Para-xylene | 60 ± 19 | 75 ± 18 | 58 ± 10 |
| 36. Ortho-xylene | 66 ± 20 | 56 ± 16 | 48 ± 8 |
| Surrogates | | | |
| Bromochloromethane | 111 ± 24 | 175 ± 14 | 112 ± 15 |
| 1,4-Difluorobenzene | 54 ± 13 | 77 ± 10 | 48 ± 7 |
| Chlorobenzene-d5 | 63 ± 15 | 50 ± 10 | 34 ± 5 |
| 1,4-dichlorobenzene | 79 ± 13 | 17 ± 4 | 22 ± 4 |
| 1,2-dichloroethane | 98 ± 9 | 91 ± 16 | 73 ± 4 |
| Toluene-d8 | 50 ± 14 | 62 ± 15 | 39 ± 4 |
| Bromofluorobenzene | 73 ± 19 | 29 ± 12 | 30 ± 3 |

[a]Results are for 10 min. distillations times, and condenser temperature held at −10° C. A 30 meter, 1 micron stabilized wax 0.53 mm bore column was used foil chromatography. Standards were replicated two to three times. Each analyte was spiked at 50 ppb concentrations.
[b]Five gram soil sample spiked with standards and with 5 ml water added to make slurry.
[c]Five gram soil sample + 1 g of cod liver oil spiked using 0.2 ml water as solvent.
[d]Five gram soil sample + 1 g of cod liver oil spiked as above with 5 ml of water added to make slurry.
[e]Interference by co-eluting hydrocarbons prevented accurate quantitation
[f]contamination prevented assessment.

TABLE 6

METHOD DETECTION LIMITS (MDL) FOR VOLATILE ORGANIC ANALYTES[a] IN WATER

| | | Method Detection Limits[a] PPb | |
|---|---|---|---|
| Analytes | CAS Number | External Standard Method | Internal[b] Standard Method |
| 1. Chloromethane | 74-87-3 | 3.1 | 2.7 |
| 2. Bromomethane | 74-83-9 | 2.5 | 1.9 |
| 3. Vinyl Chloride | 75-01-4 | 4.0 | 2.6 |
| 4. Chloroethane | 75-00-3 | 6.1 | 5.6 |
| 5. Methylene Chloride | 75-09-2 | 3.1 | 3.0 |
| 6. Acetone | 67-64-1 | 33.[c] | 33.[c] |
| 7. Carbon Disulfide | 75-15-0 | 2.5 | 1.9 |
| 8. 1,1-Dichloroethene | 75-35-4 | 3.4 | 2.8 |
| 9. 1,1-Dichloroethane | 75-35-3 | 2.3 | 2.4 |
| 10. trans-1,2-Dichloroethene | 156-60-5 | 3.0 | 2.1 |
| Cis-1,2-dichloroethene | | 2.4 | 2.4 |
| 11. Chloroform | 67-66-3 | 2.7 | 2.5 |
| 12. 1,2-Dichloroethane | 107-06-2 | 1.6 | 2.4 |
| 13. 2-Butanone | 78-93-3 | 57.[c] | 59.[c] |
| 14. 1,1,1-Trichloroethane | 71-55-6 | 1.6 | 1.9 |
| 15. Carbon Tetrachloride | 56-23-5 | 1.5 | 1.9 |
| 16. Vinyl Acetate | 108-05-4 | 23.c | 25.[c] |
| 17. Bromodichloromethane | 75-27-4 | 2.0 | 2.1 |
| 18. 1,1,2,2-Tetrachloroethane | 79-34-5 | 3.6 | 2.8 |
| 19. 1,2-Dichloropropane | 78-87-5 | 2.9 | 2.5 |
| 20. trans-1,3-Dichloro-propene | 10061-02-6 | 2.3 | 1.9 |
| 21. Trichloroethene | 79-01-6 | 2.5 | 1.7 |
| 22. Dibromochloromethane | 124-48-1 | 2.1 | 1.9 |
| 23. 1,1,2-Trichloroethane | 79-00-5 | 2.7 | 2.4 |
| 24. Benzene | 71-43-2 | 1.7 | 1.3 |
| 25. cis-1,3-Dichloro-propene | 10061-01-5 | 2.1 | 1.7 |
| 26. Bromoform | 75-25-2 | 2.3 | 2.1 |
| 27. 2-Hexanone | 591-78-6 | 4.6 | 4.7 |
| 28. 4-Methyl-2-pentanone | 108-10-1 | 3.8 | 3.7 |
| 29. Tetrachloroethene | 127-18-4 | 1.8 | 1.8 |
| 30. Toluene | 108-88-3 | 1.8 | 1.8 |
| 31. Chlorobenzene | 108-90-7 | 2.4 | 1.9 |
| 32. Ethyl Benzene | 100-41-4 | 2.4 | 1.8 |
| 33. Styrene | 100-42-5 | 2.0 | 1.8 |
| 34. Para Xylene | | 2.3 | 1.8 |

TABLE 6-continued

METHOD DETECTION LIMITS (MDL) FOR VOLATILE ORGANIC ANALYTES[a] IN WATER

| | | Method Detection Limits[a] PPb | |
|---|---|---|---|
| Analytes | CAS Number | External Standard Method | Internal[b] Standard Method |
| 25. Ortho Xylene | | 2.4 | 1.9 |

[a]Method detection limits are the average MDL's for three non-consecutive-day studies. These studies were seven replicated analyses of 5 mL aliquots of 4 ppb water. Daily MDL's were three times the precision error. Quantification was performed by GC/MS and separation with a 30 meter, stabilized wax 1 micron film thickness and 0.53 mm bore.
[b]d3-Vinylchloride used as internal standard.
[c]Method detection limits estimated using 50 ppb standards replicated five times over a single day.

TABLE 7

METHOD DETECTION LIMITS (MDL) FOR VOLATILE ORGANIC ANALYTES IN SOIL[a]

| Analytes | MDL (ppb) External Standard Method[b] | MDL (ppb) Internal Standard Method[b] |
|---|---|---|
| 1. Chloromethane | 8.6[c] | 8.2[c] |
| 2. Bromomethane | 4.9[c] | 4.8[c] |
| 3. Vinyl Chloride | 7.1[c] | 6.3[c] |
| 4. Chloroethane | 7.5[c] | 6.2[c] |
| 5. Methylene Chloride | 3.3 | 4.0 |
| 6. Acetone | Cont[d] | Cont |
| 7. Carbon Disulfide | 3.2 | 2.3 |
| 8. 1,1-Dichloroethene | 3.8 | 3.1 |
| 9. 1,1-Dichloroethane | 1.7 | 2.1 |
| 10. trans-1,2-Dichloroethene | 3.2 | 2.2 |
| 11. Cis-1,2-Dichloroethene | 2.7 | 2.0 |
| 12. Chloroform | 2.6 | 1.9 |
| 13. 1,2-Dichloroethane | 1.7 | 1.6 |
| 14. 2-Butanone | 24[e] | N/A[e] |
| 15. 1,1,1-Trichloroethane | 2.4 | 1.7 |
| 16. Carbon Tetrachloride | 1.7 | 1.5 |
| 17. Vinyl Acetate | N/A | N/A |
| 18. Bromodichloromethane | 2.3 | 1.4 |
| 19. 1,1,2,2-Tetrachloroethane | 3.2 | 2.0 |
| 20. 1,2 Dichloropropane | 3.7 | 3.0 |
| 21. trans-1,3-Dichloropropene | 2.4 | 1.8 |
| 22. Trichloroethene | 3.0 | 1.7 |
| 23. Dibromochloromethane | 2.9 | 1.5 |
| 24. 1,1,2-trichloroethane | 2.8 | 1.5 |
| 25. Benzene | 2.9 | 1.6 |
| 26. Cis-1,3-Dichloropropene | 2.5 | 1.6 |
| 27. Bromoform | 2.5 | 1.5 |
| 28. 2-Hexanone | 4.6 | 3.3 |
| 29. 4-Methyl-2-pentanone | 3.9 | 4.4[c] |
| 30. Tetrachlorethene | 2.6 | 1.4 |
| 31. Toluene | 4.4[c] | 3.4 |
| 32. Chlorobenzene | 2.6 | 1.3 |
| 33. Ethylbenzene | 4.1 | 2.8 |
| 34. Styrene | 2.5 | 1.3 |
| 35. Para-xylene | 3.9 | 2.9 |
| 36. Ortho-xylene | 4.1[c] | 3.5 |
| Surrogates | | |
| 1,2-dichloroethane | 1.8 | 1.8 |
| Toluene-d8 | 2.4 | 1.3 |
| Bromofluorobenzene | 1.9 | 1.5 |

[a]Results are for 10 min. distillations times, and condenser temperature held at −10° C. A 30 meter, 1 micron stabilized wax 0.53 mm bore column was used for chromatography.
[b]Method detection limits are the average MDL's for three non-consecutive-day studies. These studies were seven replicated analyses of 5 ml aliquots of 4 ppb soil. Daily MDL's were three times the precision error. Quantification was performed by GC/MS and separation with a 30 M stable wax micron film thickness and 0.53 mm bore.
[c]MDL exceed concentration studies.
[d]Sample contaminated with analyte.
[e]Method detection limits estimated using 50 ppb standards replicated five times over a single day.

What is claimed is:

1. An apparatus comprising a sample chamber, a sole condensing means for selectively condensing distillate, a cryotrap for sample focussing, a vacuum pump, a source of inert gas, a gaseous compound detection means and valve means for connecting said condenser column, said vacuum pump, said source of inert gas, said cryotrap and said gaseous compound detection means;

said sole condensing means consisting essentially of a single condenser column having temperature regulation means for continually sensing, adjusting and maintaining the temperature of the condenser column, said valve means having at least two positions, a loading position and an injection position, wherein when said valve means is in the loading position, said sample chamber is fluidly connected to a first end of said condenser column, a second end of said condenser column is fluidly connected to said cryotrap, and said cryotrap is fluidly connected to said vacuum pump, wherein when said valve means is in the injection position, said source of inert gas is fluidly connected to said cryotrap and said cryotrap is fluidly connected to said gaseous compound detection means, while said sample chamber is fluidly connected to the first end of said condenser column, and the second end of said condenser column is fluidly connected to said vacuum pump without being fluidly connected to said cryotrap, wherein when said valve means is in said loading position such that said vacuum pump is fluidly connected to the cryotrap, said vacuum pump causes a vacuum distillation of compounds in a sample in said sample chamber, said compounds being trapped by said cryotrap, and wherein when said valve means is in said injection position, said compounds in said cryotrap are analyzed by said gaseous compound detection means.

2. The apparatus of claim 1 wherein said valve means includes a single six port valve which controls gas flow of volatiles from the sample chamber to said cryotrap when said valve means is in the loading position and controls gas flow of volatiles from said cryotrap to said gaseous compound detection means when said valve means is in the injection position.

3. The apparatus of claim 1 wherein said valve means is a series of valves.

4. The apparatus of claim 1 wherein said gaseous compound detection means comprises a gas chromatograph.

5. The apparatus of claim 4 wherein said gaseous compound detection means further comprises a mass spectrometer.

6. The apparatus of claim 1 wherein said temperature regulation means comprises a hollow coil through which heated or cooled fluids are carried.

7. The apparatus of claim 6 wherein said temperature regulation means further comprises temperature monitoring means for sensing the temperature of the condenser column, cooling means for cooling the fluid carried through the hollow coil, and control means for actuating said cooling means in response to the temperature of the condenser column sensed by said monitoring means.

8. The apparatus of claim 7 wherein said regulation means further comprises heating means for heating the fluid carried through the hollow coil, said heating means being actuated by said control means in response to the temperature of the condenser column sensed by said monitoring means.

9. The apparatus of claim 8 wherein said regulation means includes means for maintaining said condenser column at a first constant temperature when said valve means is in said loading position.

10. The apparatus of claim 9 wherein said regulation means includes means for maintaining said condenser column at a second constant temperature when said valve means is in said injection position.

11. In an apparatus with a sample chamber, a sole condensing means for selectively condensing distillate, a cryotrap for sample focussing, a vacuum pump, a valve means and a gaseous compound detection means, wherein the sample container is fluidly connected to the sole condensing means which is in turn fluidly connected to the cryotrap which is in turn is fluidly connected to a vacuum pump when said valve means is in a first position and the cryotrap is fluidly connected to said gaseous compound detection means when said valve means is in a second position, the improvement wherein the sole condensing means consists essentially of a single condenser column located between the sample chamber and the cryotrap, said condenser column including temperature regulation means for continually sensing and adjusting the temperature of the condenser.

12. The apparatus of claim 11 wherein said temperature regulation means comprises a hollow coil through which heated or cooled fluids are carried.

13. The apparatus of claim 12 wherein said temperature regulation means further comprises temperature monitoring means for sensing the temperature of the condenser column, cooling means for cooling the fluid carried through the hollow coil, and control means for actuating said cooling means in response to the temperature of the condenser column being sensed by said monitoring means.

14. The apparatus of claim 13 wherein said regulation means further comprises heating means for heating the fluid carried through the hollow coil, said heating means being actuated by said control means in response to the temperature of the condenser column being sensed by said monitoring means.

15. The apparatus of claim 14 wherein said regulation means includes means for maintaining said condenser column at a first constant temperature when said valve means is in said loading position.

16. The apparatus of claim 15 wherein said regulation means includes means for maintaining said condenser column at a second constant temperature when said valve means is in said injection position.

* * * * *